United States Patent [19]

Delameter

[11] Patent Number: 4,597,982

[45] Date of Patent: Jul. 1, 1986

[54] METHOD FOR PROCESSING FLEXIBLE SHEETS

[76] Inventor: William D. Delameter, 1944 Eddy St., San Francisco, Calif. 94115

[21] Appl. No.: 549,400

[22] Filed: Nov. 7, 1983

Related U.S. Application Data

[63] Continuation-in-part of Ser. No. 359,589, Mar. 18, 1982, abandoned.

[51] Int. Cl.$^4$ .................. A01G 5/00; A01N 1/02; G01N 1/00; G01N 1/30
[52] U.S. Cl. ............................. 427/2; 156/57; 156/60; 350/534; 350/536; 424/3; 427/4
[58] Field of Search ............ 350/534, 535, 536; 427/2, 4; 424/3; 156/57, 60, 99, 108, 278, 295

[56] References Cited

U.S. PATENT DOCUMENTS

| | | | |
|---|---|---|---|
| 3,532,412 | 10/1970 | Miller | 350/536 |
| 3,551,023 | 12/1970 | Brackett | 350/536 |
| 4,302,480 | 11/1981 | Fischer et al. | 156/57 X |

Primary Examiner—Michael R. Lusignan
Attorney, Agent, or Firm—Townsend and Townsend

[57] ABSTRACT

A method is described for applying liquid to flexible sheets, as in staining medical specimens afixed to thin flexible slides. In platen staining methods, flexible slides are centrally curved downward by the attraction of liquid between the slide and platen, thereby damaging the specimen. The invention prevents this damage by placing a glass slide on top of the flexible slide and interjecting a liquid such as alcohol in between. The flexible slide, which acts as a barrier between the two liquid layers, is pulled upward from a platen by the attraction to the overlying liquid.

12 Claims, 2 Drawing Figures

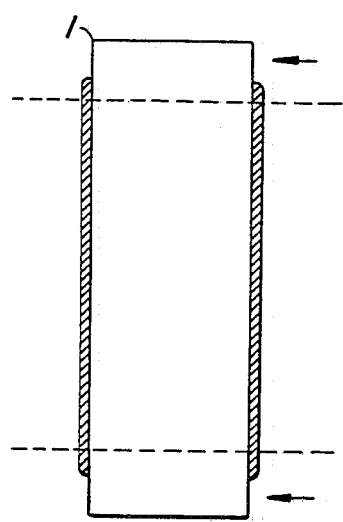
FIG._1.
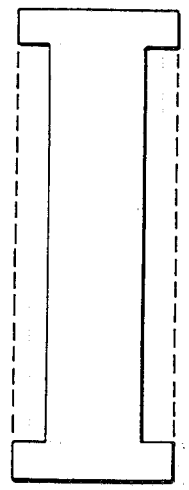
FIG._2.

METHOD FOR PROCESSING FLEXIBLE SHEETS

CROSS REFERENCE TO CORRESPONDING APPLICATION

This application is a continuation in part application of the parent application:
 title: Apparatus and Method for Processing Medical Specimens on Plastic Sheets.
 filed: 03/18/82
 Ser. No.: 06/359,589, now abandoned.

FIELD OF INVENTION

The invention relates generally to applying liquid to flexible sheets, and specifically to staining medical specimens on flexible slides.

STATEMENT OF PRIOR ART

The prior art that I am aware of has been described and is identical to that in the parent application, Apparatus and Method for Processing Medical Specimens on Plastic Sheets, Ser. No. 06/359,589, filed 03/18/82; examiner, Henry, J., G.A.U. 257. If required, additional copies of the materials will be readily supplied.

DISCUSSION OF PRIOR ART

Currently, medical specimens are smeared centrally on glass slides, conventionally about 1 inch by 3 inches in dimensions, and fixed to the slide by dipping in an alcohol or other appropriate fixing solution, and then processed by staining sequentially by dipping in solutions or by staining on a platen. While thin plastic slides have many advantages over glass in lessened weight, cost, size, and breakage, one barrier to their use has been finding suitable ways of staining flexible slides. Because traditional glass slides have been in such widespread use, it is important that methods of staining flexible slides be compatible with methodologies used for glass slides. While manual staining methods can be compatible they are time consuming. Reel methods, as are used in photographic film developing, tend to be incompatible with rigid glass slides and therefore require a separate machine—uneconomical in both cost and space. One machine in widespread use for staining medical specimens on glass slides utilizes two helical screws to propel the rigid glass slides over a platen, rather than moving a platen under the slides as on rollers, and solutions are applied sequentially between the platen and the moving slides. Because the solutions are applied only to the gap between the platen and one side of the slide, and drawn in between by capillary attraction, this method conserves solutions even though consistently fresh solutions are used to flood the specimen on each individual slide. While flexible plastic in the shape of a glass slide will pass through such a platen stainer, the generally curved nature of such a flexible slide, though slight, defeats such methodology for delicate and precious medical specimens. This is because, although specimens are firmly adherent to slides when dry, specimen smears are easily scratched off when wet; and because flexible slides are pulled downward to the platen by the attraction of the underlying liquids, whereupon the platen or dirt on the platen scratches off specimen on the surface of the flexed slide.

While methods utilizing adhesives or glue to flatten a flexible slide to a glass slide may be adequate to prevent scratching, they introduce an additional component. An adhesive only method would require coating or pre-coating, care to create and maintain smooth surfaces especially in the area where the specimen is smeared, & that the adhesives be kept from chemicals that might affect character. While these problems may be overcome, this approach has been covered in the parent application, and the invention describes a simpler methodology.

It is an object of the present invention to provide an improved method for processing flexible sheets.

Another object of the invention is to make practical the use of flexible medical slides by providing an enabling method of processing flexible slides without need of specialized equipment.

Further objects and advantages of my invention will become apparent from a consideration of the drawings and ensuing description thereof.

BRIEF DESCRIPTION OF DRAWINGS

FIG. 1 shows a top view of a flexible slide that is slightly wider than a glass slide over a platen. Section lines indicate an underlying platen. Unshaded area shows dimensions of a 1" by 3" glass slide. Arrows show points and direction of applied motive force.

FIG. 2 shows a top view of a carrier which is narrower over a platen than a flexible slide in the shape of a 1" by 3" glass slide. Broken lines indicate the 1" width of the flexible slide.

DESCRIPTION OF THE INVENTION

The invention makes use of a novel method of reversing or counteracting the bending of a flexible slide so that a centrally smeared specimen is held away from a platen. A liquid is interjected between a rigid backing plate, such as a glass slide, and a flexible slide before the specimen side of the flexible slide is placed in contact with liquid on the platen. The attraction of the liquid above the flexible slide counteracts the attraction of the liquid below the flexible slide thereby preventing contact between the platen and the specimen on the flexible slide. The preferred design is such that the flexible slide acts as a barrier between the two liquid layers. This is accomplished by designing the backing plate to be slightly smaller in dimensions over the platen than the flexible sheet. Because the edges of the backing plate are receded from the edges of the flexible sheet, the liquid of the backing plate exerts its attraction more centrally to the flexible sheet than does the attraction of the platen liquid, tending to pull the central portion of the flexible slide upward. The liquids above and below the flexible sheet may be applied by various means such as nozzles attached to metered pumps or by wicks adjacent to the gaps through capillary attraction.

In the method as adapted to a platen staining machine in widespread use in clinical laboratories, the flexible slides would be dipped in alcohol and the backing plate applied before the alcohol evaporated, thereby creating a sandwiched liquid layer protected from evaporation between the flexible slide and the backing plate. This step corresponds to current methods of dipping glass slides in alcohol or fixing solutions prior to staining. The flexible slide is then placed on the platen and processed as an ordinary slide would be processed.

After staining and drying the specimen, the flexible slide may be examined dry or the arrangement can fit on an ordinary microscope slide stage with the alcohol still acting as a binder. After examination, the flexible slide and glass slide would be separated, allowing the alcohol to evaporate and the flexible slide to be stored. A solution such as microscopy oil, with the same index of refraction as glass, might be substituted for the alcohol. The alcohol could be allowed to evaporate, or not be applied to the uppermost side of the slide, and oil interjected before processing. Similarly, a transparent glue like material, or mounting medium, might be used to form a permanent bond between the flexible slide and microscope slide, especially for specimens which might be examined repeatedly.

FIG. 1 shows the preferred embodiment of the invention wherein an ordinary glass slide can be used as a backing plate. The unshaded central portion is the approximate area of a glass slide. The one inch width of the narrowed ends keeps the slide centered if motive force is applied at points shown by arrows, keeping the shaded areas of the flexible slide in place as a barrier. Because some slide holding stages may slightly overlap the glass slide and compress the corners, and bend the slide, the corners (1) may be rounded off or the unshaded area be reduced to slightly less than one inch by three inches.

FIG. 2 shows a special carrier for use if the dimensions of the flexible slide are the same as those of a 1" by 3" glass slide. The edges of the backing plate again are receded from the flexible slide edges and the underlying liquid stays beneath the flexible slide.

In another embodiment, wherein the backing plate and flexible sheet could be of the same dimensions, coatings of liquid repellent material such as boron nitride on the backing plate or along the edges of the flexible sheets, would prevent capillary attraction from drawing the underlying liquid into the exposed gap between the backing plate and flexible sheet.

Similarly, a glue or adhesive edging around the area of the specimen could seal off and prevent the uncontrolled intermingling of the fluids above and below the flexible sheet.

For small, irregularly shaped plastic sheets, rather than adjusting the backing plate surface to be less than that of of the plastic sheet, the sheet might be glued to a larger, standardized, sheet and becoming an integral part of the longer sheet be stained by the same methods.

While the above description contains many specifications, these should not be construed as limitations on the scope of the invention, but rather as an exemplification of one preferred embodiment thereof. Many other variations are possible, for example in photographic film processing, applying coatings to small flexible sheets, and using the layer between the flexible sheet and the backing plate for processing. Accordingly, the scope of the invention should be determined not only by the embodiment illustrated, but by the appended claims and their legal equivalents.

What is claimed is:

1. A method of applying processing liquid from a flat platen to a biological specimen on the first face of a flexible sheet having first and second faces, said method comprising the steps of:
   (a) joining said second face of said sheet to one face of a rigid flat plane to fix said sheet in a substantially planar configuration; and
   (b) drawing said first face of said sheet over said platen while maintaining a substantially constant gap therebetween, said gap being filled with said processing liquid and sufficiently narrow to retain said processing liquid therein by capillary attraction, thereby wetting said first face of said sheet with said processing liquid.

2. A method according to claim 1 in which step (a) is achieved by applying glue to said faces to form a permanent bond therebetween.

3. A method according to claim 1 in which said rigid flat plate is optically transparent, and step (a) is achieved by applying glue to said faces to form a permanent bond therebetween which is optically transparent.

4. A method according to claim 1 in which step (a) is achieved by a film of a second liquid located between said faces to cause said faces to adhere by capillary attraction.

5. A method according to claim 4 in which said film is applied by placing said faces in contact and injecting said second liquid therebetween.

6. A method according to claim 4 in which said film is applied by applying said second liquid to at least one of said faces and placing said faces in contact while said film is wet.

7. A method according to claim 4 in which said second liquid is sufficiently volatile to evaporate from said sheet upon separation of said sheet from said rigid flat plate.

8. A method according to claim 4 in which said second liquid is selected from the group consisting of alcohol and microscopy oil.

9. A method according to claim 4 in which said flexible sheet and said rigid flat plate are of substantially the same lateral dimensions and a continuous strip of coating material repellent to at least one of said liquids is applied along the perimeter of either said flexible sheet, said rigid flat plate or both on the face at which said sheet and plate are joined to prevent intermingling of said liquids.

10. A method according to claim 4 in which said flexible sheet and said rigid flat plate are of substantially the same lateral dimensions and a continuous strip of glue or adhesive repellent to said processing liquid is applied to said first face of said flexible sheet to encircle said specimen and to prevent intermingling of said liquids.

11. A method according to claim 4 in which said flexible sheet extends beyond said rigid flat plate along all edges of said sheet which are in contact with said processing liquid, by a sufficient distance to prevent intermingling of said liquids.

12. A method of applying processing liquid from a flat platen to a biological specimen on the first face of a substantially rectangular flexible sheet having first and second faces, said method comprising the steps of:
   (a) dipping said sheet in a second liquid which evaporates upon exposure to air;
   (b) placing said second face of said sheet while still wetted with said second liquid in contact with one face of a rigid flat plate to cause said faces to adhere by capillary attraction, the width of said plate being less than the width of said sheet thereby leaving an exposed strip along each longitudinal side of said sheet; and
   (c) drawing said first face of said sheet over said platen while maintaining a substantially constant gap therebetween, said gap being filled with said processing liquid and sufficiently narrow to retain said processing liquid and sufficiently narrow to retain said processing liquid therein by capillary attraction, thereby wetting said specimen with said processing liquid.

* * * * *